United States Patent [19]

Lehky et al.

[11] Patent Number: 5,082,777
[45] Date of Patent: * Jan. 21, 1992

[54] PROCESS FOR THE PRODUCTION OF 6-HYDROXYNICOTINIC ACID

[75] Inventors: Pavel Lehky, Naters; Hans Kulla; Stephane Mischler, both of Visp, all of Switzerland

[73] Assignee: Lonza Ltd., Switzerland

[*] Notice: The portion of the term of this patent subsequent to Apr. 19, 2005 has been disclaimed.

[21] Appl. No.: 701,507

[22] Filed: Feb. 14, 1985

[30] Foreign Application Priority Data

Feb. 21, 1984 [CH] Switzerland .................. 825/84

[51] Int. Cl.$^5$ .................. C12P 17/12; C12N 1/20; H01R 13/24; H01R 4/48
[52] U.S. Cl. .................. 435/122; 435/824; 435/832; 435/874; 435/877; 435/252.1; 435/252.5; 435/253.3
[58] Field of Search .............. 435/122, 253, 824, 832, 435/874, 877

[56] References Cited

U.S. PATENT DOCUMENTS 4,038,993  8/1977  Geiss et al. .................. 435/877

FOREIGN PATENT DOCUMENTS 644847  8/1984  Switzerland .................. 435/122

OTHER PUBLICATIONS

Briaucourt et al., J. Chim. Ther. (1973), 8 (2), pp. 226–232.
Allison, M. J. C., Biol. Chem. (1943), 147, p. 785.
Behrman, E. J., and Stanier, R. V., J. Biol. Chem. (1957) 228, p. 923.
Hunt, A. L., Biochem. J. (1958), 72, pp. 1–7.
Ensign and Rittenberg, J. Biol. Chem., 239 (1964), pp. 2285–2291.

*Primary Examiner*—Douglas W. Robinson
*Assistant Examiner*—J. Weber
*Attorney, Agent, or Firm*—Fisher, Christen & Sabol

[57] ABSTRACT

Process for the production of 6-hydroxynicotinic acid from nicotinic acid. The hydroxylation is carried out enzymatically in the presence of a microorganism of the species Pseudomonas, Bacillus or Achromobacter, for example, *Achromobacter xylosoxydans*. Preferably the enzymatic hydroxylation is carried out at 20° to 40° C. and a pH of 5.5 to 9.0 under aerobic conditions. Also, preferably a 0.1 percent by weight solution up to a saturated (preferably a 0.5 to 10 percent by weight) nicotine acid solution is used.

8 Claims, No Drawings

PROCESS FOR THE PRODUCTION OF 6-HYDROXYNICOTINIC ACID

BACKGROUND OF THE INVENTION

1. Field Of The Invention

The invention relates to a process for the production of 6-hydroxynicotinic acid by the enzymatic hydroxylation of nicotinic acid.

2. Prior Art

Several methods are known for the production of 6-hydroxynicotinic acid by means of organic synthesis. For example, 6-hydroxynicotinic acid can be obtained from 2-pyridone by the Kolbe-Schmidt type carboxylation of hydroxy aromatics. Other syntheses start out from maleic acid or isocinchomeronic acid [Briancourt et al., J. Chim. Ther. (1973), 8 (2) 226–32; Quarroz, Swiss Application No. 7731/80]. However, none of such synthesis permit a simple, inexpensive and favorable-to-the-environment type of production of pure 6-hydroxynicotinic acid. Such processes have the disadvantage that the conversion is not quantitative and undesirable by-products accompany the reaction. The by-products represent contamination which must be removed from the reaction product after reaction is completed.

It is also known that microorganisms of the variety Bacillus, Pseudomonas, Clostridium, Sarcina and Mycobacterium grew on nicotinic acid and that they use such substrate as a source of carbon, nitrogen and energy [Allison, M. J. C., J. Biol. Chem. (1943) 147, 785; Behrman, E. J., and Stanier, R. V., J. Biol. Chem. (1957) 228, 923]. In the case of all of such studied organisms, the nicotinic acid is oxidized to 6-hydroxynicotinic acid in the first decomposition step. The 6-hydroxynicotinic acid is further immediately converted, and without significant enrichment, in the case of aerobic organisms, to water, carbon and ammonia.

After break up of the microorganism, it is possible to isolate the nicotinic acid hydroxylase into more or less pure form [Hunt, A. L., Biochem. J. (1958) 72, 1–7]. The nicotinic acid hydroxylases are large molecules of approximately 400,000 dalton. They contain flavin co-factors, many metal atoms (Fe, Mo), inorganic sulfur and in some cases even selenium. The nicotinic acid hydroxylases are active only in the presence of suitable electron transmitting systems (for example, cytochrome, flavins, $NADP^+$ and others). The nicotinic acid hydroxylase can be isolated from cell extracts and the enzyme preparations can be used for the hydroxylation of nicotinic acid. Such has been done and small quantities of 6-hydroxynicotinic acid were actually obtained [Behrman and Stanier, J. Biol. Chem. (1957) 228, 923]. Apart from the high costs of enzyme isolation and of the instability of the nicotinic acid hydroxylase, it was still necessary to take care of the regeneration of cofactors and electron transmitting systems.

BROAD DESCRIPTION OF THE INVENTION

An object of the invention is to provide a process which overcomes the above-stated disadvantages of the prior art. Another object of the invention is to provide a process with which, in an economic manner, 6-hydroxynicotinic acid can be produced from nicotinic acid with very high purity and yield. Other objects and advantages are set out herein or are obvious herefrom to one skilled in the art.

The advantages and objects of the invention are achieved by the process of the invention.

This invention involves a process for the production of 6-hydroxynicotinic acid. The process includes enzymatically hydroxylating nicotinic acid in the presence of a microorganism of the species Pseudomonas, Bacillus or Achromobacter. Preferably the microorganism is an *Achromobacter xylosoxydans,* and most preferably is the *Achromobacter xylosoxydans* having the designation DSM 2783. The enzymatic hydroxylation preferably is carried out at 20° to 40° C. and a pH of 5.5 to 9.0 under aerobic conditions. Also preferably the nicotinic acid is used in the form of a 0.1 percent by weight nicotinic acid (aqueous) solution up to a saturated nicotinic acid (aqueous) solution. Most preferably a 0.5 to 10 percent by weight nicotinic (aqueous solution) is used.

DETAILED DESCRIPTION OF THE INVENTION

As used herein, all parts, ratios, percentages and proportions are on a weight basis unless otherwise stated herein or otherwise obvious herefrom to one ordinarily skilled in the art.

It has been found that microorganisms of the varieties Pseudomonas, Bacillus and Achromobacter permit successful production of 6-hydroxynicotinic acid. Very effectively, *Achromobacter xylosoxydans* DSM 2402, *Pseudomonas putida* NCIP 10521 or a Bacillus strain [which was described by Ensign and Rittenberg, J. Biol. Chem. 239, (1964) 2285–2291] is used. But preferably the new strain *Achromobacter xylosoxydans* DSM 2783 is used.

The taxonomic description (to the extend presently known) of the new strain *Achromobacter xylosoxydans* DSM is as follows: Name: *Achromobacter xylosoxydans* DSM No. 2783 Isolated from: nicotinic acid mother lye

(A) Morphology

Cultivation in nutrient broth
(1) cell shape small rods 2 to 3.5 $\mu$ long, approximately 0.6 $\mu$ wide
(2) arrangement: individually
(3) motility: strongly movable; peritrically flagellated
(4) endospore: none
(5) gram: negative
(6) oxidase: positive
(7) catalase: positive
(8) strictly aerobic Such new strain agrees in all tested characteristic with the type strain of *Achromobacter xylosoxydans* DSM 2402, with the exception of hydrolysis of acetamide.

The cited strains of *Achromobacter xylosoxydans* are deposited at the German collection of microorganisms (DSM), Gesellschaft für Biotechnologische Forschung mbH., Griesebachstrasse 8, 4300 Göttingen, Federal Republic of Germany, under numbers DSM 2402 and DSM 2783.

The new strain *Achromobacter xylosoxydans* DSM 2783 was deposited on November 18, 1983, in the German collection of microorganisms (DSM), Gesellschaft fur Biotechnologische Forschung mgH., Griesebachstrasse 8, 4300 Gottingen, Federal Republic of Germany, under the designation or number DSM 2783. Such deposit of a culture of such new strain of microorganism in such depository affords permanence of the deposit and ready accessibility thereto by the public if a patent is granted, under conditions which assure (a) that access to the culture will be available during pendency of the patent application to one determined by the Commissioner to be entitled thereto under 37 C.F.R. 1.14 and 35 U.S.C. 122, and (b) that all restrictions on the availability to the public of the culture so deposited will be irrevocably removed upon the granting of the patent. The applicants or their assigns have provided assurance of permanent availability of the culture to the public through such depository.

The strains *Pseudomonas putida* NCIP 10521 and 8176 can readily be obtained at the National Collection of Industrial Bacteria, Torry Research Station 135 Abbey Road, Aberdeen AB98DC, Scotland. The strain *Achromobacter xylosoxydans* DMS 2402 can readily be obtained at the above-mentioned West German depository.

The above-mentioned strains grow with nicotinic acid as the only source for carbon, nitrogen and energy. The cultivation of the above-named microorganisms can be accomplished according to the processes known for this type of strains. For example, strain DSM 2783 is fermented in a diluted and sterilized nicotinic acid solution (0.05 to 0.5 percent by weight), which contains phosphate buffer (50 mM) pH 7.0, trace elements in the following amounts (in mg/l):

| | |
|---|---|
| $CaCl_2.2H_2O$ | 20 |
| $MnSO_4$ | 10 |
| $FeSO_4.7H_2O$ | 5 |
| $CoCl_2.6H_2O$ | 0.1 |
| $CuSO_4.5H_2O$ | 0.1 |
| $ZnSO_4.7H_2O$ | 0.1 |
| $NaMoO_4.2H_2O$ | 0.1 |

In order to accelerate the growth, such solution contains a small quantity of yeast extract (Merck) (0.05 percent by weight), for 24 to 48 hours at 30° C. under aerobic conditions. The grown biomass (approximately 10 g of moist weight/l) is rich in nicotinic acid hydroxylase. The cells are centrifuged off and can be used immediately or after storage at −20° C. directly, that is, to say without obtaining enzyme or purification, for the subject nicotinic acid hydroxylation. For carrying out the nicotinic acid hydroxylation, it is desirable that the decomposition of the nicotinic acid does not go beyond the first step, namely, the hydroxylation to 6-hydroxynicotinic acid. In this production phase, the growth of the microorganism would take place at the expense of the yield.

The following parameters, which are important for the economy of the nicotinic acid hydroxylation, have to be fulfilled:

(a) The cells should grow no more (consumption of nicotinic acid).

(b) The nicotinic acid hydroxylase should remain active.

(c) The path of decomposition of the nicotinic acid should be broken off at the step of the 6-hydroxynicotinic acid production.

(d) The product (6-hydroxynicotinic acid) is to be excreted from the cell.

Surprisingly, it has been found that these parameters are fulfilled simultaneously whenever the concentration of the nicotinic acid is increased in the reaction medium. This favorable behavior for the production of the 6-hydroxynicotinic acid seems to be widely spread in the microbic metabolism. It is assumed that the sequential enzyme (6-hydroxynicotinic acid hydroxylase) is inhibited by high nicotinic acid concentrations.

As mentioned above, the strain *Anchromobacter xylosoxydans* DSM 2783 preferably grows in diluted nicotinic acid solutions (0.05 to 0.5 percent by weight) and at the same time completely consumes the given nicotinic acid. With an increasing concentration of the nicotinic acid, the growth of the cell is impeded and, at above 2 percent by weight of nicotinic acid concentration, no growth can be observed. The activity of the nicotinic acid hydroxylase, however, remains unchanged in the cells.

The reaction of the enzymatic hydroxylation takes place advantageously at 20° to 40° C. and at a pH of 5.5 to 9.0 under aerobic conditions. Effectively, 0.1 percent by weight up to saturated (preferably 0.5 to 10 percent by weight of) nicotinic acid solutions are used. The nicotinic acid can also be used in the form of alkali salt solutions.

The catabolic decomposition is interrupted after the hydroxylation step; therefore, the side and secondary reactions are eliminated and the purity and yield of the 6-hydroxynicotinic acid are very high. A further positive characteristic of the microorganisms examined is that they excrete the product of the hydroxylation, that is, the 6-hydroxynicotinic acid, into the solution. This considerably simplifies the isolation of the product. After the separation of the cells from the reaction broth by centrifuging or microfiltration, the clear solution is acidified. The white 6-hydroxynicotinic acid obtained thereby is filtered off and dried.

By way of summary, 6-hydroxynicotinic acid is produced by the enzymatic hydroxylation of nicotinic acid in the presence of a microorganism of the variety Pseudomonas, Bacillus or Achromobacter and especially of an *Achromobacter xylosoxydans* having the designation DSM 2783.

In the examples, for practical considerations, the laboratory type production of the 6-hydroxynicotinic acid for a one molar quantity was separated into two steps, namely:

Step 1: Production of the biomass with high NS-hydroxylase activity

Step 2: Enzymatic hydroxylation of the nicotinic acid.

Of course, if desired, the two steps can be combined into one, that is, a so-called single pot process, without any difficulty.

EXAMPLE 1

(Step 1) Production of the Acromobacter xylosoxydans DSM 2783 biomass.

A nutrient solution which, in 4750 ml, contained 51.9 g of $Na_2HPO_4.2H_2O$, 20.0 g of $KH_2PO_4$, 2.5 g of yeast extract and 10 g of nicotinic acid was placed into a fermentor and was sterilized for 20 minutes at 120° C. After cooling to 30° C., a sterile solution of the above-mentioned trace elements was added. The fermentor was inoculated with 500 ml of a starter culture (same composition) and was fermented at 30° C. and pH 7.0, while gassing it with air for 24 hours. After 24 hours, 200 ml of a solution of 10 g of nicotinic acid and 2.5 g of yeast extract in water was added under sterile conditions and the fermentation was continued. After 42 hours, the culture was harvested and the cells were separated by centrifuging (30 minutes at 15,000 g). 38.3 g of moist biomass was obtained.

(Step 2) Hydroxylation of the nicotinic acid.

A 3-liter reaction vessel was filled with 2250 ml of 5 percent sodium nicotinate solution (pH 6.5) and was heated to 30° C. A suspension of *Achromobacter xylosoxydans* DSM 2783 cells in 120 ml of water was added and the reaction mixture was aerated intensively while stirring it well. The pH, the temperature and the oxygen concentration in the reaction mixture were measured and regulated continuously. After 7 hours, the concentration of the dissolved oxygen rose. At this point, the reaction was completed. The reaction suspension was centrifuged off and the cells in the sediment were used for the next charge. The clear supernatant was brought to pH 1.5 with concentrated sulfuric acid and the 6-hydroxynicotinic acid obtained was drained off and dried. 121 g of white product was obtained which, according to HPLC analysis, contained 98.6 percent of 6-hydroxynicotinic acid. This corresponded to a 6-hydroxynicotinic acid yield of 93.7 percent, related to the nicotinic acid used.

EXAMPLE 2

(Step 1) Production of the *Pseudomonas putida* NCIB 10521 biomass.

1 liter of the same nutrient solution which is described in Example 1 was sterilized in a 2-liter flask and, after cooling to 30° C., was inoculated with a *Pseudomonas putida* NCIB 10521 culture from an agar plate. The culture was shaken for 48 hours in the breeding box at 30° C. After reaching the maximum cell density, the cells were centrifuged off during 20 minutes at 10,000 g. The cells were suspended in 10 ml of phosphate buffer (50 mM, pH 7).

(Step 2) Hydroxylation of the nicotinic acid.

A 1-liter shaking flask was filled with 100 ml of neutral 40 mM sodium nicotinate solution, and 10 ml of cell suspension (from step 1) was added thereto. The mixture was shaken intensively in the breeding box for 90 minutes at 30° C. The cells were centrifuged off and the clear excess (108 ml) was analyzed for nicotine and 6-hydroxynicotinic acid. According to HPLC analysis, the solution contained 36.1 mM of 6-hydroxynicotinic acid (Na-salt). This corresponds to a yield of 97.5 percent, calculated on the basis of the nicotinic acid used. The concentration of the nicotinic acid was deeper than 0.2 percent of the 6-hydroxynicotinic acid concentration. The solid 6-hydroxynicotinic acid was isolated from the solution by acidifying with a strong acid.

EXAMPLE 3

(Step 1) Production of the *Pseudomonas putida* NCIP 8176 biomass.

*Pseudomonas putida* cells, using the procedure of Example 1, step 1, were fermented. 45.3 g of a moist biomass were obtained.

(Step 2) Hydroxylation of the nicotinic acid.

A 3-liter reaction vessel was filled with 1125 ml of 10 percent sodium nicotinate solution (pH 7.0) and was heated to 35° C. The suspension of *Pseudomonas putida* NCIP 8176 biomass in 100 ml of water was added and the reaction mixture was intensively aerated while stirring well. The pH, the temperature and the oxygen concentration in the reaction mixture were measured and regulated continuously (pH =7.0; temperature=35° C.; $pO_2$=5 mg/l). After 5 hours and 20 minutes, the concentration of the dissolved oxygen rose in one jump to 7 mg/l. At this point, the reaction was completed. The reaction suspension was filtered using an Amicon Hollow Fiber HIMO1-43 filter. The strongly concentrated (50 x) cell suspension was used for the next charge. The clear residue was brought to pH 1.5 with concentrated hydrochloric acid. The precipitated snow-white 6-hydroxynicotinic acid was subjected to suction, washed with water on the filter and dried under vacuum (20 mbar; 60° C.; 10 hours). 122.3 g of a white product was obtained which, according to HPLC analysis, contained 99.2 percent of 6-hydroxynicotinic acid. This corresponds to a 6-hydroxynicotinic acid yield of 95.4 percent, related to the nicotinic acid used.

What is claimed is:

1. A biologically pure culture of *Achromobacter xylosoxydans* DSM 2783, which is capable of specific enzymatic hydroxylation of nicotinic acid to 6-hydroxynicotinic acid.

2. Process for the production of 6-hydroxynicotinic acid comprising enzymatically hydroxylating nicotinic acid in an aqueous medium containing *Achromobacter xylosoxydans* DSM 2783 to 6-hydroxynicotinic acid at a pH and a temperature which are effective to achieve such enzymatic hydroxylation, the concentration of the nicotinic acid in the aqueous admixture being such that is effective to substantially prevent the enzymatic conversion of the 6-hydroxynicotinic acid.

3. Process as claimed in claim 2 wherein the enzymatic hydroxylation is carried out at 20° to 40° C. and a pH of 5.5 to 9.0 under aerobic conditions.

4. Process as claimed in claim 3 wherein the concentration of the nicotinic acid is from 0.5 percent by weight, based on the weight of the aqueous admixture, up to a saturated nicotinic acid solution.

5. Process as claimed in claim 3 wherein the concentration of the nicotinic acid is 0.5 to 10 percent by weight, based on the weight of the aqueous solution.

6. Process for the production of 6-hydroxynicotinic acid comprising enzymatically hydroxylating nicotinic acid in an aqueous medium containing the microorganism *Achromobacter xylosoxydns* DSM 2402 at 20° to 40° C. and a pH of 5.5 to 9.0 under aerobic conditions, the concentration of the nicotinic acid being 0.5 to 10 percent by weight, based on the weight of the aqueous solution, which is effective to substantially prevent the enzymatic conversion of the 6-hydroxynicotinic acid.

7. Process for the production of 6-hydroxynicotinic acid comprising enzymatically hydroxylating nicotinic acid in an aqueous medium containing the microorganism *Pseudomonas putida* NCIP 10521 at 20° to 40° C. and a pH of 5.5 to 9.0 under aerobic conditions, the concentration of the nicotinic acid being 0.5 to 10 percent by weight, based on the weight of the aqueous solution, which is effective to substantially prevent the enzymatic conversion for the 6-hydroxynicotinic acid.

8. Process for the production of 6-hydroxynicotinic acid comprising enzymatically hydroxylating nicotinic acid in an aqueous medium containing the microorganism *Pseudomonas putida* NCIP 8176 at 20° to 40 ° C. and a pH of 5.5 to 9.0 under aerobic conditions, the concentration of the nicotinic acid is 0.5 to 10 percent by weight, based on the weight of the aqueous solution, which is effective to substantially prevent the enzymatic conversion of the 6-hydroxynicotinic acid.

* * * * *